United States Patent [19]

Zasuwa

[11] Patent Number: 4,531,941

[45] Date of Patent: Jul. 30, 1985

[54] METHOD AND APPARATUS FOR ADMINISTERING BLOOD

[75] Inventor: Gerard A. Zasuwa, Redford, Mich.

[73] Assignee: Henry Ford Hospital, Detroit, Mich.

[21] Appl. No.: 655,299

[22] Filed: Sep. 26, 1984

Related U.S. Application Data

[63] Continuation of Ser. No. 415,817, Sep. 8, 1982, abandoned.

[51] Int. Cl.³ .................. A61M 5/00; A61M 1/03
[52] U.S. Cl. ........................... 604/113; 128/400; 422/46
[58] Field of Search ............... 604/113–114; 128/399–400, DIG. 3; 165/163; 422/46

[56] References Cited

U.S. PATENT DOCUMENTS

| | | | |
|---|---|---|---|
| 2,876,769 | 3/1959 | Cordova | 128/DIG. 3 |
| 3,103,928 | 9/1963 | Broman | 128/DIG. 3 |
| 3,370,153 | 2/1968 | Du Fresne | 604/114 X |
| 3,856,475 | 12/1974 | Marx | 422/46 |
| 4,160,801 | 7/1979 | Badolato et al. | 165/163 X |
| 4,376,095 | 3/1983 | Hasegawa | 422/46 |

Primary Examiner—Dalton L. Truluck
Attorney, Agent, or Firm—Barnes, Kisselle, Raisch, Choate, Whittemore & Hulbert

[57] ABSTRACT

A method and apparatus for administering large quantities of blood which has been stored at less than ambient temperatures continuously and rapidly to a patient at physiologically acceptable temperatures and pressures in a short time wherein the blood is continuously directed through a plurality of discrete capillary paths in heat-exchange relationship with a warming medium, the number of said paths being such that the pressure of the blood is not substantially increased, and the blood is rapidly administered directly to a patient.

5 Claims, 7 Drawing Figures

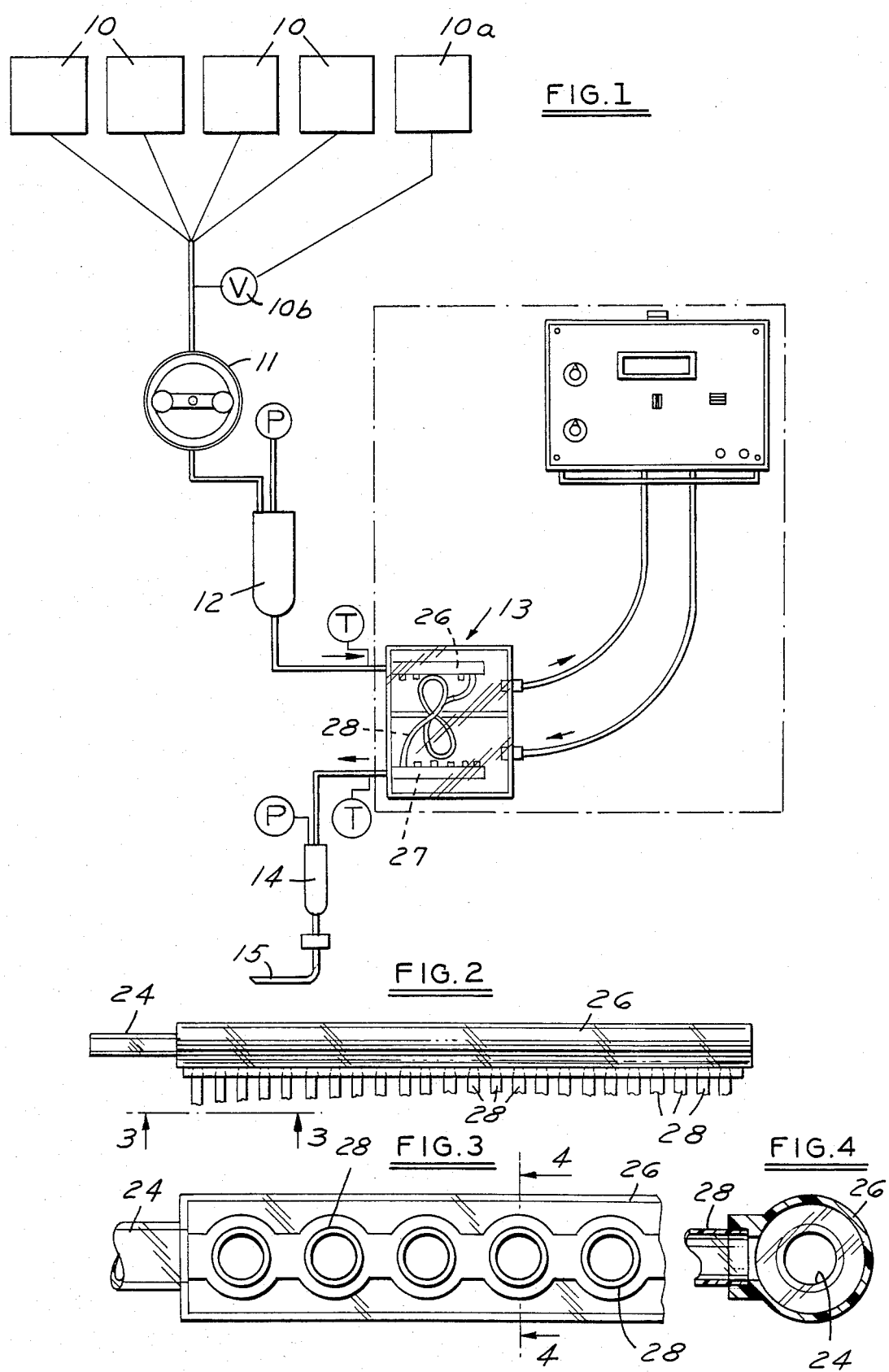

METHOD AND APPARATUS FOR ADMINISTERING BLOOD

This application is a continuation of application Ser. No. 415,817, filed Sept. 8, 1982, now abandoned.

This invention relates to blood transfusions and particularly to a method and apparatus for rapidly raising the temperature of blood in order that large quantities can be administered in a short time.

BACKGROUND AND SUMMARY OF THE INVENTION

In traumatically injured patients, hemorrhagic patients, and surgery patients, it is known that large quantities of blood should preferably be administered in a short time at body temperature. Inasmuch as whole blood is normally stored at lower temperatures such as 4° C., it is difficult to warm such blood in sufficient quantities as required. In one prior method, blood is dripped into patients by gravity and forced by pressure through blood warming coils placed in a reservoir of water warmed with a heating element. In this technique, the infusion rate is not greater than 25 ml/min. This method requires about 30 minutes to administer a single unit of whole blood.

In another method that has been proposed, microwave heaters are provided which may cause red cell destruction. Efforts to increase the rate of heating in the method of warming through coils also causes red cell destruction and possible rupture of the coils.

In accordance with the invention, the method and apparatus for administering large quantities of blood which has been stored at less than ambient temperatures continuously and rapidly to a patient at physiologically acceptable temperatures and pressures in a short time comprises directing blood through a plurality of discrete capillary paths in heat-exchange relationship with a warming medium, the number of said paths being such that the pressure of the blood is not substantially increased, and the blood is rapidly administered directly to a patient.

DESCRIPTION OF THE DRAWINGS

FIG. 1 is a schematic diagram of the method and apparatus embodying the invention.

FIG. 2 is a fragmentary view on an enlarged scale showing a portion of the apparatus.

FIG. 3 is a fragmentary view taken along the line 3—3 on an enlarged scale.

FIG. 4 is a fragmentary sectional view taken along the line 4—4 in FIG. 3.

DESCRIPTION

Figure 5:
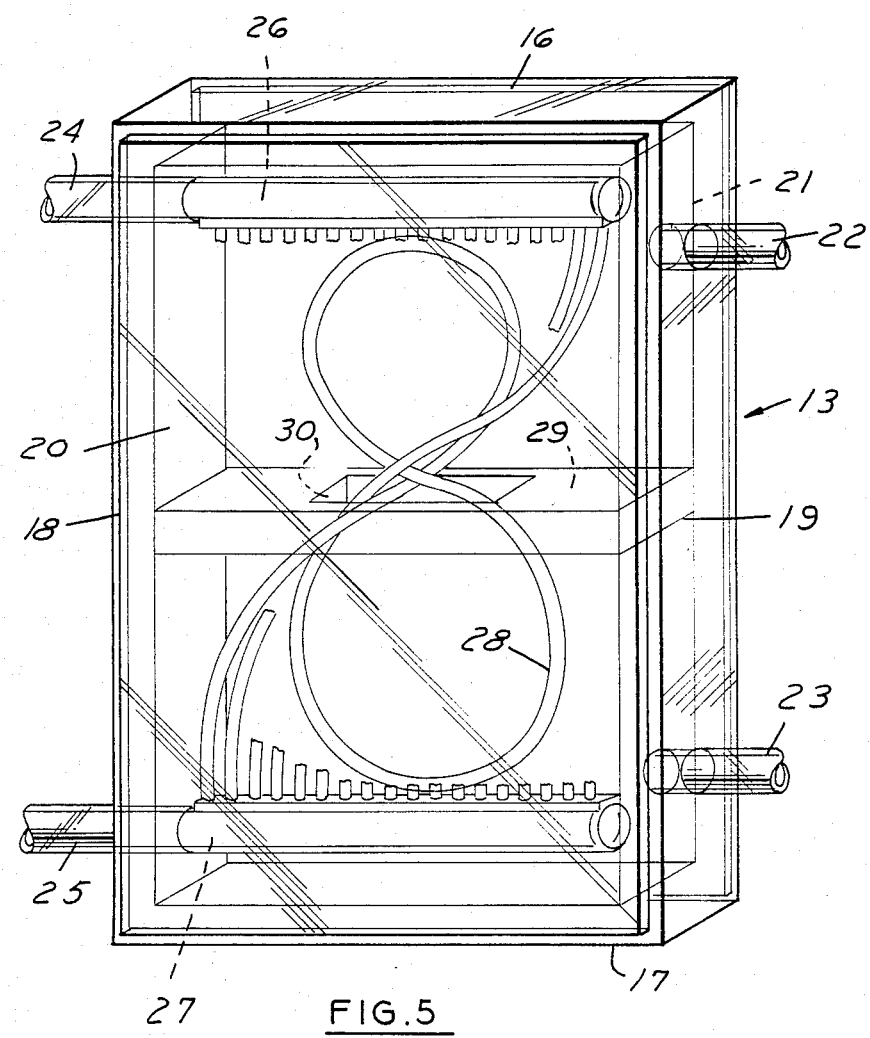
FIG. 5 is a perspective view of a portion of the apparatus.

Referring to FIG. 1, the method and apparatus embodying the invention comprises directing the stored blood which is at a lower refrigeration temperature (i.e. 4° C.) having been refrigerated from a plurality of sources 10 by a pump 11 to a drip chamber 12 and then, in turn, to a heat exchanger device 13 to a drip chamber 14 and then through a line 15 at venous pressure directly and rapidly to the patient. An air bubble detector 15 is provided in line 15, in accordance with common practice and functions to shut off flow if air bubbles or foam are present. A line extends from a saline source 10a through a valve 10b for purging the system prior to passage of the blood.

Referring to FIG. 5, the heat exchanging apparatus 13 comprises a generally rectangular housing having a top wall 16, a bottom wall 17, side walls 18, 19, a front wall 20, and a rear wall 21. The housing further includes a first inlet 22 for introducing a warming medium such as a saline or water solution and a first outlet 23 for removing the saline solution. The housing further includes a second inlet 24 for blood and a second outlet 25 for blood. Means are provided within the medium to direct the blood in a plurality of discrete capillary paths in heat exchange relationship with the warming medium. This comprises spaced manifolds or headers 26, 27 and a plurality of discrete tubes 28 connected to the manifolds 26, 27. The tubes are made of inert, non-toxic plastic such as silicone rubber, made and sold by Dow Chemical Company under the trademark Silastic. The manifolds are both preferably made of plastic similar to tubes 28 and are connected to one another by fusing the tubes into the headers in the manner shown in FIGS. 2 and 3.

The tubes have ultra thin walls. The cross section of the passage through the tubes preferably ranges between 0.05 and 0.06 inch and the wall thickness ranges between 0.025 and 0.030 inch. In a preferred arrangement, the tubes have an internal diameter of 0.062 inch and an external diameter of 0.095 inch.

The length of the tubes is substantially greater than the distance between the two headers 26, 27 and an internal wall 28 is provided dividing the housing into two parts, the wall having an opening 29. The tubes are arranged in a figure-8 pattern passing through the opening 29. The wall with the opening 29 insures a good circulation of the warming medium from the first inlet 22 to the second outlet 23.

The term capillary as used herein means thin walled tubing having a small internal diameter to define a film of blood flowing in laminar fashion in heat-exchange relation to the warming medium.

Inlets 22, 23 are connected by tubes to a warming device 30 which functions to provide a medium such as a saline or water solution. The device 30 controls the saline bath temperature at the desired temperature, preferably 40° and delivers it to the heat exchanging apparatus 13.

Figure 7:
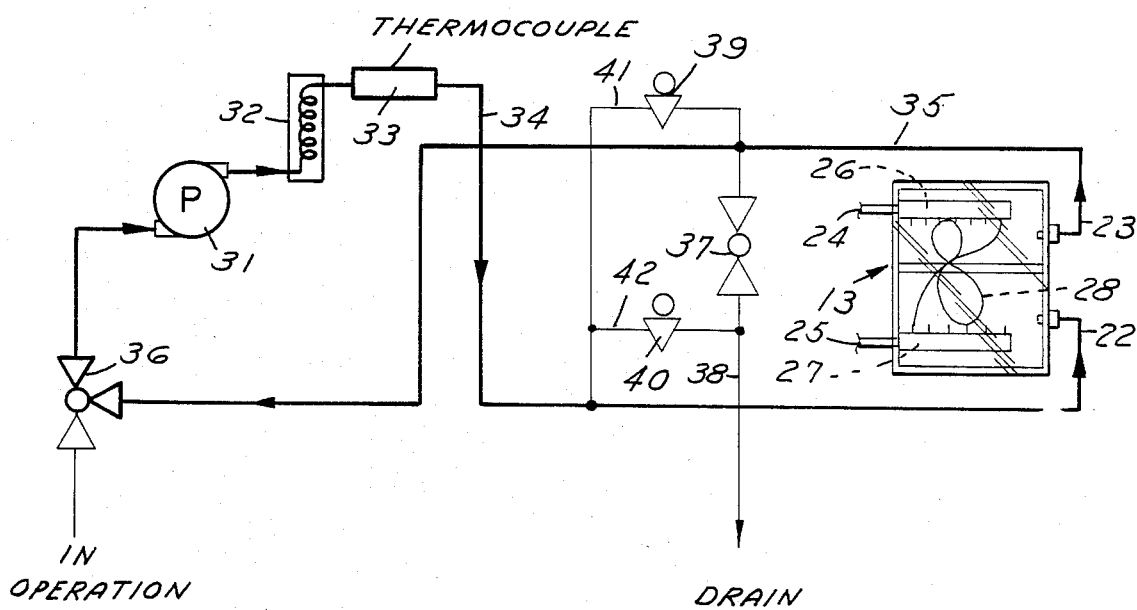
FIG. 7 is a hydraulic diagram similar to FIG. 6 showing the flow during operation.

Referring to FIG. 7, the warming device 30 comprises a closed loop system including a pump 31 that pumps the warming medium such as the saline solution through a heater 32 that is controlled by a thermocouple 33 and delivers the medium to a line 34 to the linet 22 of the heat exchanging apparatus 13 and then from the outlet 23 the saline solution is returned to a line 35 and through a three-way solenoid valve 36 to the inlet of the pump 31.

Figure 6:
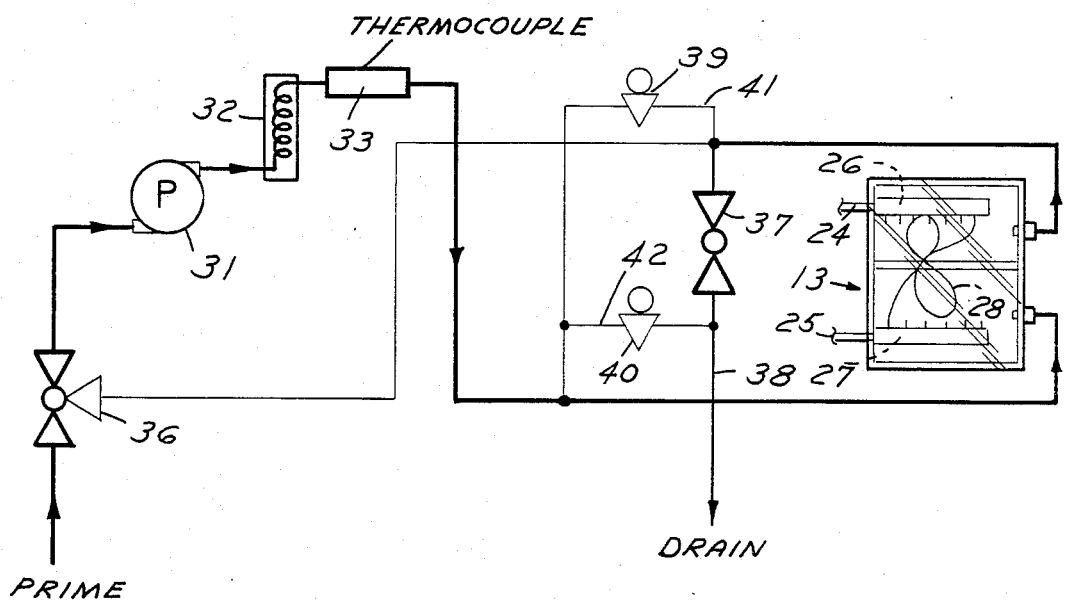
FIG. 6 is a hydraulic diagram of the warming medium portion of the apparatus showing the flow during priming.

Referring to FIG. 6, in order to prime the circuit, the three-way valve 36 is opened permitting additional fluid to be provided and pumped through the heat exchanging apparatus 13 and then through a two-way solenoid valve 37 in a bypass line 38 to drain unitl the system is filled.

Pressure relief valves 39, 40 and associated lines 41, 42 are provided upstream and downstream of the valve 37 and function to relieve the pressure to drain if it exceeds a predetermined value or if kinking of lines 41, 42 occurs.

It has been found that in use substantial quantities of blood can be heated without adverse effect on the blood and delivered directly and rapidly at low pressure to the patient. For example, blood can be supplied at normal physiological temperature of 37.2° C. after being heated from 4° C. and at a rate of flow of 200 ml/min.

In order to control the flow and rate of temperature exchange, pressure sensors and temperature sensors are provided at the inlet and outlet to heat exchanging apparatus 13 as shown in FIG. 1.

Typical experimental results that have been achieved with the method and apparatus are as follows:

| TRIAL | T IN | T OUT | BFL | T OF WARMING FLUID |
|---|---|---|---|---|
| 1 | 25.5 | 37.0 | 100 | 38.5 |
| 2 | 16.3 | 36.0 | 150 | 38.5 |
| 3 | 21.0 | 35.8 | 100 | 38.5 |
| 4 | 22.0 | 35.8 | 100 | 38.5 |
| 5 | 16.0 | 36.8 | 100 | 39.0 |
| 6 | 10.2 | 36.8 | 200 | 40.0 |
| 7 | 10.2 | 37.0 | 200 | 40.0 |

Where T = temperature in degrees Centigrade
BFL = flow of blood out of heat-exchanging apparatus in ml/min.

Laboratory tests on some of the blood trials indicated the following:

| TRIAL | WBC | RBC | HGB | HCT | MCV | MCH | MCHC | PLT | NA | K |
|---|---|---|---|---|---|---|---|---|---|---|
| PRE 3 | 3.60 | 3.80 | 11.8 | 33.6 | 87.8 | 30.8 | 35.1 | 94. | 153 | 4.69 |
| POST 3 | 4.30 | 4.34 | 13.2 | 38.2 | 87.9 | 30.5 | 34.7 | 106 | 152 | 5.51 |
| PRE 4 | 9.00 | 3.83 | 12.7 | 38.3 | 100. | 33.3 | 33.2 | 298 | XXX | XXXX |
| POST 4 | 9.00 | 3.95 | 13.3 | 39.7 | 100. | 33.7 | 33.0 | 271 | 145 | 8.46 |
| PRE 5 | 3.20 | 3.38 | 10.3 | 32.3 | 94.0 | 30.6 | 32.3 | N.D. | 152 | 3.08 |
| POST 5 | 4.00 | 4.27 | 13.2 | 40.7 | 94.0 | 31.0 | 32.7 | N.D. | 153 | 1.60 |
| PRE 6 | 4.80 | 3.22 | 9.10 | 28.0 | 87.0 | 28.1 | 32.6 | N.D. | 143 | 20.1 |
| POST 6 | 6.40 | 4.27 | 12.3 | 37.2 | 87.0 | 28.8 | 33.4 | N.D. | 140 | 19.9 |
| PRE 7 | 2.40 | 4.60 | 13.2 | 40.3 | 87.6 | 28.7 | 32.8 | 123 | 137 | 22.0 |
| POST 7 | 2.10 | 4.63 | 13.4 | 40.7 | 87.7 | 29.1 | 33.1 | 96. | 137 | 22.0 |

Wherein:
PRE = before entering the heat-exchange apparatus
POST = after leaving the heat-exchanging apparatus
WBC = white blood cell count
RBC = red blood cell count
HGB = hemoglobin count
HCT = hematocrit
MCV = mean corpuscular volume
MCH = mean corpuscular hemoglobin
MCHC = mean corpuscular hemoglobin concentration
PLT = platelets
NA = sodium
K = potassium

I claim:

1. An apparatus for rapidly raising the temperature of blood from a storage temperature of about 4° C. to body temperature in order that large quantities can be administered in a short time comprising
   a housing of generally rectangular configuration having a top wall, a bottom wall, side walls, a front wall and a rear wall,
   said housing including a first inlet for warming medium in a side wall thereof and a first outlet in a side wall thereof for removing the warming medium,
   said housing including a second inlet in a side wall thereof for receiving blood and a second outlet in a side wall thereof for removing blood,
   a first manifold connected to said second inlet and extending within said housing,
   a second manifold connected to said second outlet and extending within said housing in generally parallel relation to said first manifold,
   a plurality of discrete tubes within said housing,
   each said tube having one end connected to said first manifold at longitudinally spaced points along said first manifold and the other end connected to said second manifold at longitudinally spaced points along said second manifold,
   an internal wall extending between said side walls, and front and back walls of said housing and dividing the housing in two parts, the first manifold being positioned in one part and the second manifold being positioned in the other part,
   said second inlet, said second outlet, said first and second manifolds, said tubes and said internal wall being made of an inert, non-toxic plastic,
   said internal wall having an opening therethrough,
   the length of said tubes being substantially greater than the distance between the first and second headers and the tubes being arranged in a figure-8 pattern passing through the opening of the internal wall, such that as the warming fluid flows from the first inlet to the first outlet, it is directed over the entire length of the tubes through which the blood to be warmed is flowing.

2. The apparatus set forth in claim 1 wherein the cross section of the passage through the tubes ranges between 0.05 and 0.06 inch.

3. The apparatus set forth in claim 2 wherein the wall thickness of the tubes ranges between 0.025 and 0.030 inch.

4. The apparatus set forth in claim 2 including a warming device connected to the first inlet and second inlet and constructed and arranged for holding the temperature of the warming medium supplied to the apparatus at about 40° C.

5. The apparatus set forth in claim 1 including a pump for receiving the blood from a source and directing it to the second inlet.

* * * * *